(12) United States Patent
Mori et al.

(10) Patent No.: US 7,361,785 B2
(45) Date of Patent: Apr. 22, 2008

(54) COMPOUND PROTECTING AGAINST ULTRAVIOLET RAYS

(75) Inventors: Masao Mori, Toyama (JP); Haruo Saito, Toyama (JP); Masako Nakagawa, Chiba (JP); Atsushi Nishida, Chiba (JP)

(73) Assignee: Lead Chemical Co., Ltd., Toyama (JP)

( * ) Notice: Subject to any disclaimer, the term of this patent is extended or adjusted under 35 U.S.C. 154(b) by 169 days.

(21) Appl. No.: 10/533,202

(22) PCT Filed: Nov. 5, 2002

(86) PCT No.: PCT/JP02/11517

§ 371 (c)(1),
(2), (4) Date: Jun. 23, 2005

(87) PCT Pub. No.: WO2004/041771

PCT Pub. Date: May 21, 2004

(65) Prior Publication Data

US 2006/0051303 A1    Mar. 9, 2006

(51) Int. Cl.
*C07C 63/36* (2006.01)
*C07C 205/06* (2006.01)

(52) U.S. Cl. .................. 562/490; 462/436; 462/438; 462/460; 424/47

(58) Field of Classification Search .......... 562/436, 562/438, 460, 490; 424/47
See application file for complete search history.

(56) References Cited

U.S. PATENT DOCUMENTS

| | | | | |
|---|---|---|---|---|
| 3,175,950 A | * | 3/1965 | Abraham et al. | ............ 424/60 |
| 4,536,346 A | * | 8/1985 | Shepherd et al. | ........... 558/414 |
| 4,937,370 A | * | 6/1990 | Sabatelli | ...................... 560/45 |
| 5,229,107 A | * | 7/1993 | Sabatelli et al. | ............. 424/59 |

FOREIGN PATENT DOCUMENTS

| | | |
|---|---|---|
| DE | 581329 | 7/1933 |
| EP | 0 251 398 A2 | 1/1987 |
| EP | 0 542 941 | 5/1993 |
| FR | 2315908 | 1/1977 |
| JP | 57157884 * | 9/1983 |
| JP | 62-223155 * | 1/1987 |
| JP | A 6-501489 | 2/1994 |
| JP | A 6-501490 | 2/1994 |
| WO | WO 92/19208 | 11/1992 |

OTHER PUBLICATIONS

Fichter, Fr., et al. "Studies on Unsaturated Acids. V. On Crotonyltouylenediamine" 1907, vol. 74, Abstract from CAPLUS.*
Barra, M., et al., "Inhibition of hydrolysis of p-nitrophenyl esters by association with an erythromycin A derivative" 1992, vol. 7, Abstract from CAPLUS.*
Whitehead, C., "Diuretics. Organomercurials", 1958, Journal of the American Chemical Society, vol. 80, pp. 2179, 2181-2182.*
Kulickova et al., "Physicochemical study of 3'- and 4'-substituted 2-hydroxy-5-methylbenzophenone", 1979, vol. 33(5), Abstract from CAPLUS.*
Saharia et al.: "Hydroxy ketones. VII. Fries reaction of the esters of o- and m-methoxybenzoic acids and a study of the mechanism" Journal of Scientific & Industrial Research, 1957, pp. 125-128.
Whitehead: "Diuretics Organomercurials", Journal of the American Chemical Society, 1958, p. 2181.
Babin: "Sur quelques derives vinylogues de l' acetyl salicylique", Societe De Pharmacie De Bordeaux, 1974, pp. 61-67.
Georgiyants et al.: "Michael Addition of N, N'-Dibenzylmalonamide to N-Aryl (alkyl)crotonamides", Russian Journal of Organic Chemistry, vol. 38, No. 3, 2002, pp. 475-476.
Maksudov et al.: "alpha.—and .beta. -Naphthyl esters of some .alpha., .beta. -unsaturated acids," Uzbekskii Khimicheskii Zhurnal, 1975, pp. 34-36 (Abstract Only).
Starkov et al.: "Condensation of cinnamic acid with phenols, cresols, xylenols, and their methyl ethers", Izvestiya Vysshikh Uchebnykh Zavedenii, Khimiya 1 Khimicheskaya Teknologiya, 1977, pp. 1149-1155 (Abstract Only).
Spratt et al.: "P-fluorobenzoyl chloride for characterization of active hydrogen functional groups by fluorine-19 nuclear magnetic resonance spectrometry", Analytical Chemistry, 1984, pp. 2038-2043.
Gibson et al.: "Cleavage of halobenzophenones by potassamide in ammonia. New routes to xanthem- and thioxanthem-9-ones", Journal of the Chemical Society 1975 (Abstract Only).
Williams et al.: "Hydrolysis of acyl chymotrypsins", Journal of the Chemical Society, 1971, pp. 2401-2406 (Abstract Only).
Bowie et al.: "Electron-impact studies. LXX. Substituent effects in the negative-ion spectra of nitroaryl esters", Organic Mass Spectrometry, 1972 (Abstract Only).
Nishinaga et al.: "Base-catalyzed oxygenolysis of 3-hydroxyflavones", Journal of the Chemical Society, 1979 (Abstract Only).

* cited by examiner

*Primary Examiner*—Yvonne Eyler
*Assistant Examiner*—Yate' K Cutliff
(74) *Attorney, Agent, or Firm*—Oliff & Berridge, PLC

(57) ABSTRACT

An ultraviolet ray protection agent including a compound having an ultraviolet ray protection effect as an active ingredient. The compound is expressed by general formula I':

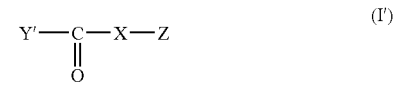

wherein X represents NH or O; Y' represents a vinyl group substituted by a methyl group or a phenyl group, or a phenyl group substituted by a methoxy group or a fluorine atom, or a naphthyl group; and Z represents a phenyl group substituted by a methyl group, a carboxyl group or a nitro group, or a naphthyl group. The compound represented by the general formula I' includes both novel compounds of the present invention and known compounds. The ultraviolet ray protection agent of the present invention offers outstanding ultraviolet ray protection effectiveness and is very safe.

6 Claims, No Drawings

COMPOUND PROTECTING AGAINST ULTRAVIOLET RAYS

FIELD OF THE INVENTION

The present invention relates to a compound that protects against ultraviolet rays and an ultraviolet ray protection agent including the compound as an active ingredient.

BACKGROUND OF THE INVENTION

Recently, destruction of the ozone layer that acts as a barrier layer protecting against ultraviolet rays from the sun has been occurring along with the progression of global scale environmental changes. As a result, the bare skin of people has become exposed to strong ultraviolet (UV) rays from the sun. These UV rays include high amounts of energy and have a variety of harmful effects on the skin. Thus, attention has focused on the function of UV ray protection agents that are used for sun care protection of the skin against harmful UV rays.

As people go about their everyday lives their skin is often exposed, regardless of whether they are indoors or outside. In particular, when working outside or doing sports, leisure activities or the like, people have a tendency to expose their skin for various reasons, such as to attain a feeling of coolness (to cool the skin) or a feeling of freedom. As a result, there is a danger that people will expose their skin to harmful UV rays from the sun throughout the year.

In order to protect against the danger of skin cancer developing and harmful reactions of the body (said to be a cause of skin aging) caused by exposure to the UV rays, cosmetic products are used (for example, sunscreen creams) made of compounds of UV ray protection agents. The UV ray protection agents that are used as compounds in these types of cosmetic product can be broadly classified as being either organic type UV ray protection agents or inorganic type UV ray scattering agents.

Organic type UV ray protection agents have conjugated double bonds in their molecules. This type of molecule absorbs the light energy of the UV rays, and changes it in to a different form of energy like heat energy. If the molecular structure of the agent is changed, the wave length of the UV rays that are maximally absorbed changes (the maximum absorption wavelength). As a result, organic type UV protection agents are classified based on the difference in the UV ray absorption region that they are intended to absorb, namely, as UVB absorption agents that absorb UV rays with a comparatively short wavelength (maximum absorption wavelength of 280 to 320 nm), and UVA absorption agents that absorbs UV rays with a comparatively long wavelength (maximum absorption wavelength of 320 to 400 nm).

On the other hand, inorganic type UV ray scattering agents are metallic oxides, most famously represented by titanium dioxide, that scatter the UV rays with their high refractive index.

However, inorganic type UV ray scattering agents epitomized by titanium dioxide generally have a color from white to light yellow, and act so as to strongly conceal the surface of the object to which they are applied. Accordingly, for example, if a sunscreen cream or the like including inorganic type UV ray scattering agent is applied to the skin to protect against sunburn, the skin becomes an unnatural color with a white tone. Thus, for example, if a person wishes to protect against sunburn but wishes to avoid having an unnatural white toned skin color, it is difficult to use large quantities of just an inorganic type UV ray scattering agent.

In contrast to this, organic type UV ray protection agents are generally colorless, or have a slight coloring. They either have no concealing effect on the surface of the object to which they are applied, or have a concealing effect that can be ignored.

Accordingly, if a person wishes to protect their skin against the harmful action of UV rays while also avoiding their skin from becoming an unnatural white toned color, it is desirable to use either an organic type UV ray protection agent or a compound including a favorable mixing ratio of an organic type UV ray protection agent and an inorganic type UV ray scattering agent.

Organic type UV ray protection agents have the advantage that it is possible to obtain different UV ray protection effects for different uses by changing the molecular structure thereof.

At present, p-methoxycinnamic acid-2-ethyl hexyl and 4-tert-butyl4'-methoxy-dibenzoylmethane are widely used, respectively, as UVB absorption agent and UVA absorption agent.

However, conventional organic type UV ray protection agents like this generally have a strong skin irritant effect and acute toxicity. Since UV ray protection agents are usually used by spreading them over a large area of the skin, it is preferable that skin irritant effect and acute toxicity are as low as possible. Moreover, bearing in mind the recent increase in the amount of UV rays from the sun, a substantial increase in the UV ray protection performance of UV ray protection agents is desirable. Further, the UV ray protection agent is exposed to direct sunlight over a long period after it has been applied to the skin, and thus it is important that it has high resistance to decomposition by light and heat.

Based on a general assessment of all these matters, it is clear that conventional UV ray protection agents still have inadequate performance for their role as UV ray protection agents. Accordingly, there is strong need for development of: a new compound with low toxicity (for example, skin irritation effect and acute toxicity) to the body, a high degree of safety, strong maximum absorption in the UVB region and the UVA region, and high resistance to decomposition by light and heat; and a new UV protection agent containing a compound (including the new compound) that has a UV ray protection effect as an active ingredient.

DISCLOSURE OF THE INVENTION

Through diligent research aimed at solving the above described problems of the conventional technology, the inventors have achieved the present invention by devising new compounds that have lower toxicity to the body, a higher degree of safety, and an equal or better UV ray protection effect, as compared to known compounds having a UV ray protection effect.

Moreover, in addition to these new compounds, the inventors have discovered compounds with an outstanding UV ray protection effect among known compounds that were not conventionally known to have any UV ray protection effects. The inventors have succeeded in inventing a UV ray protection agent that includes, in addition to the new compounds, the compounds (the know compounds) as an active ingredient that exhibits the UV ray protection effects.

More specifically, the present invention relates to a compound (hereinafter referred to as "i") that is expressed by following general formula I:

wherein
- X represents NH or O;
- Y represents a vinyl group substituted by a methyl group or a phenyl group, or a phenyl group substituted by a methoxy group or a fluorine atom; and
- Z represents a phenyl group substituted by a methyl group, a carboxyl group or a nitro group, or alternatively a naphthyl group, with proviso that the compound excludes a compound expressed by the following formula:

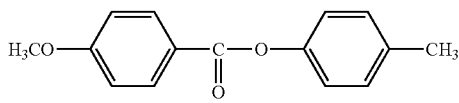

The following compounds of the present invention are preferable:

ii) A compound (compound CU-1008) expressed by the following formula expressing i of the general formula I:

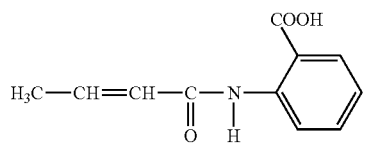

iii) A compound (compound CU-2102) expressed by the following formula expressing i of the general formula I:

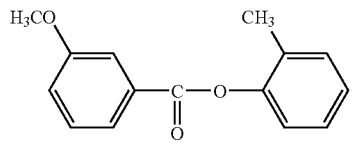

iv) A compound (compound CU-5008) expressed by the following formula expressing i of the general formula I:

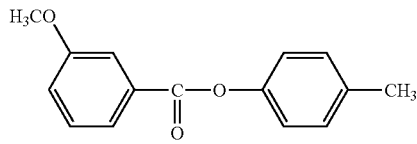

v) A compound (compound CU-9005) expressed by the following formula expressing i of the general formula I:

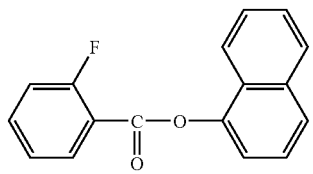

vi) A compound (compound CU-10005) expressed by the following formula expressing i of the general formula I:

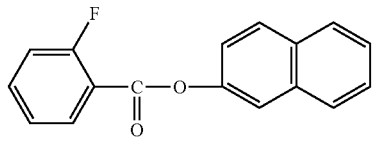

vii) A compound (compound CU-11005) expressed by the following formula expressing i of the general formula I:

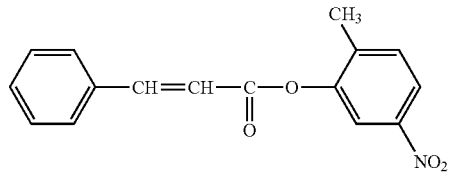

The present invention also relates to a UV ray protection agent which includes a compound having a UV ray protection effect as an active ingredient and which is expressed by the general formula I' below:

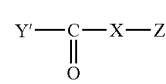

(I')

wherein
- X represents NH or O;
- Y' represents a vinyl group substituted by a methyl group or a phenyl group, or a phenyl group substituted by a methoxy group or a fluorine atom, or a naphthyl group; and
- Z represents a phenyl group substituted by a methyl group, a carboxyl group, or a nitro group, or alternatively a naphthyl group.

It is preferable that the UV ray protection agent of the present invention includes the compound expressed by the general formula I, in particular, compounds ii to vii, as an active ingredient thereof.

BEST MODE FOR CARRYING OUT THE INVENTION

Hereinafter, the compound and the UV ray protection agent of the present invention will be explained in further detail.

a) With Regard to the Compound Expressed by Formula I:
The compounds expressed by formula I (excluding the already known compound CU-5009) are new compounds that have been synthesized by the inventors for the first time. Specific examples of the compounds expressed by the formula are the previously described compounds CU-1008, CU-2102, CU-5008, CU-9005, CU-10005, and CU-11005.

b) With Regard to the Compounds Expressed by Formula I':
The compounds expressed by formula I' are the compounds expressed by formula I in the case that the definition of Y also includes naphthyl group, and also includes the known compound CU-5009 that is excluded from the definition of the compounds expressed by formula I. In addition to the compound CU-5009, know compounds CU-2010 and CU-5004, described later, are also included among the compounds expressed by formula I'. It was not known until now that compounds CU-2010, CU-5004, and CU-5009 have UV ray protection effect.

The compound expressed by formula I' is combined in a suitable quantity with a suitable base material like an ointment base (Plastibase) or an emulsion as the active ingredient of the UV ray protection agent. The favorable mixing ratio of the compound expressed by formula I' with respect to the total quantity of the UV ray protection agent is different depending on the individual type of compound expressed by formula I' and the purpose for which the UV ray protection agent is to be used (for example, how much UV ray protection effect is desired). Accordingly, a mixing ratio is selected that is suitable for the type of compound and purpose of use. The mixing ratio is, for example, 0.1 to 30 mass percent, favorably 1 to 20 mass percent, more favorably 2 to 10 mass percent, and most favorably 2.5 to 5 mass percent.

In addition to the compounds expressed by formula I' as the active ingredient, other compounds, mixtures or additives, etc. commonly used in the field of UV ray protection agents may be mixed at a desired mixing ratio in the UV ray protection agent of the present invention.

b-1) With Regard to Compound CU-2010:
* Chemical formula: $C_{18}H_{14}O_2$ (molecular weight: 262.30)
* Chemical name: o-tolyl-2-naphthyl carboxylate
* Structure:

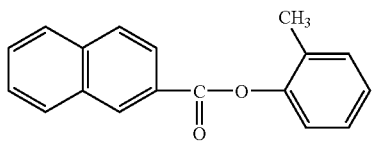

* Reference

Used as a sensitizer in heat sensitive recording sheet in which thermal coloring is caused by color forming lactone compounds and acidic substance (disclosed in Japanese Patent Laid-Open Publication No. Sho. 58-183286). Note that, there is no mention in these document that this compound has UV ray protection effect or that it can be used as a UV ray protection agent.
* Reference Document
  1) Japanese Patent Laid-Open Publication No. Sho. 58-183286 b-2) With Regard to Compound CU-5004:
Chemical formula: $C_{18}H_{14}O_2$ (molecular weight: 262.30)
Chemical name: p-tolyl-2-naphthyl carboxylate
Structure:

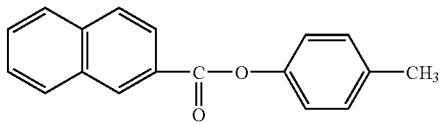

* Reference

Used as a sensitizer in heat sensitive recording sheet in which thermal coloring takes place, like compound CU-2010 described above (disclosed in Japanese Patent Laid-Open Publication No. Sho. 58-183286). Note that, there is no mention in these documents that this compound has UV ray protection effects or that it can be used as a UV ray protection agent.

Reference Documents
1) Japanese Patent Laid-Open Publication No. Sho. 58-183286
2) McAdams, Christopher L. et. al; Am. Chem. Soc. Symp. Ser. 706 (Micro- and Nano Pattering Polymers), 292-305 (1998).

b-3)
* Chemical formula: $C_{15}H_{14}O_3$ (molecular weight: 262.30)
* Chemical name: p-tolyl anisate
* Structure:

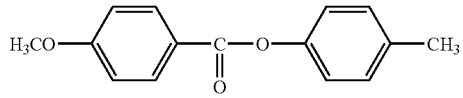

* Reference

The compound is a compound that configures an eutectic mixture of a nematic liquid crystal with electro-optic properties (disclosed in Japanese Patent Laid-Open Publication No. Sho. 57-125281) or a liquid crystal composition (disclosed in Japanese Patent Laid-Open Publication No. Sho. 58-157884). However, there is no mention in these documents that this compound has UV ray protection effect or that it can be used as a UV ray protection agent.
* Reference Documents
  1) Japanese Patent Laid-Open Publication No. Sho. 57-125281
  2) Japanese Patent Laid-Open Publication No. Sho. 58-157884
  3) Praefcke Klaus et al.; Chemical-Ztg. 101 (10), 450-451 (1977).
  4) Nikitin, K. V et al.;Mendeleev Commun. 4, 129-131 (1991).

EXAMPLES

Hereinafter examples of the present invention will be described.

I. Synthesis of the Compounds Expressed by Formula I (Excluding the Already Known Compound CU-5009)

Example 1

Synthesis of Compound CU-1008

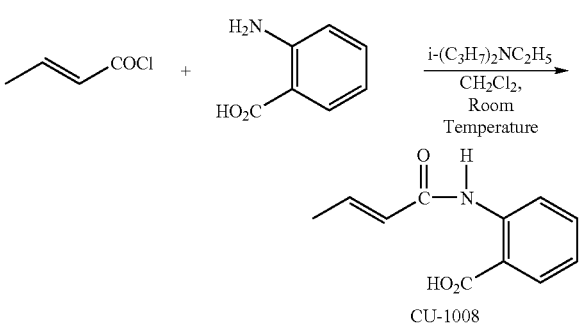

Synthesis Method

Anthranilic acid (4.00 g, 29.2 mmol) was poured in to a 100 mL round-bottomed flask, and argon substitution performed. Next, dichloromethane (50 mL) was added to the flask, and stirred at 0° C. for 20 minutes. Then, i-$C_3H_7N$ $(C_2H_5)_2$ (10.7 mL, 2.1 equivalent weight) was added to the flask, and stirred for 30 minutes. Next, trans-crotonyl chloride (3.1 mL, equivalent weight of 1.1) was added to the flask, and stirred for 3 hours at room temperature. After destruction of the base material was confirmed using thin layer chromatography (TLC), saturated chloride ammonium aqueous solution (20 mL) was added, and extracted with dichloromethane (50 mL). Following washing of the organic layer with saturated saline (20 mL), anhydrous magnesium sulfate was used for drying, and filtering carried out. The solvent was distilled off under a reduced pressure, and the obtained residue was purified using silica-gel column chromatography ($SiO_2$ 80 g, ethyl acetate/n-hexane=¼). Then, recrystallization was performed (ethyl acetate/n-hexane=1/1), and compound CU-1008 (976 mg, yield 10%) was obtained.

Physical Property Values and Spectrum Data:
i) External appearance, physical properties: Yellow needle crystal, m.p.=105 to 107° C.
ii) UV, visible: $\lambda_{max}$=234 nm, $\epsilon_{max}$=31937
iii) IR(KBr) ν $cm^{-1}$: 3483, 1761, 1661, 1598, 1447, 1445, 1317, 1283, 1254, 1222, 1040, 1012, 771
iv) $^1$H-NMR; 400 MHz ($CDCl_3$) δ ppm: 2.00 (dd, 3H, J=1.7, 7.0 Hz), 6.17 (dq, 1H, J=1.7, 15.6 Hz), 7.14 (qd, 1H, J=7.0, 15.6 Hz), 7.47 (ddd, 1H, J=1.6, 6.4, 8.2 Hz), 7.55 (d, 1H, J=8.2 Hz), 7.78 (ddd, J=1.5, 6.4, 7.9 Hz), 8.18 (dd, 1H, J=1.6, 7.9 Hz)
v) $^{13}$C-NMR; 100 MHz($CDCl_3$) δ ppm: 18.6, 116.9, 123.2, 126.8, 127.9, 128.5, 136.4, 142.2, 147.0, 156.8, 159.3
vi) LRFABMS m/z (%): 188 [100%, M-$H_2O^+$]

Example 2

Synthesis of Compound CU-2102

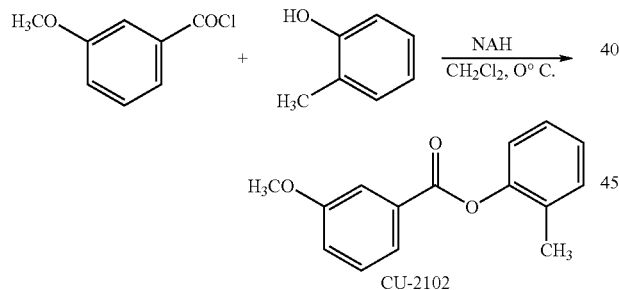

CU-2102

Synthesis Method

Ortho-cresol (0.73 mL, 7.12 mmol, 1 equivalent weight) and meta anisole chloride (1.21 g, 7.12 mmol, 1 equivalent weight) were added to a dichloromethane (10 mL) suspension of sodium hydride (0.57 g, 60 mass % liquid paraffin suspension, 14.23 mmol, 2 equivalent weight) under ice cold conditions. Following this, the reaction liquid was stirred for 1 hour under ice cold conditions. Destruction of the base material was confirmed using TLC, and then saturated chloride ammonium aqueous solution (20 mL) was added and the reaction stopped. The products were extracted three times using dichloromethane (20 mL), and the liquid extract was washed with saturated saline, and dried with anhydrous magnesium sulfate. The dried extract was concentrated under a reduced pressure, and the obtained residue was purified using silica-gel column chromatography ($SiO_2$ 40 g, ethyl acetate/n-hexane=1/10) so as to obtain compound CU-2102 (1.72 g, yield 10%).

Physical Property Values and Spectrum Data:
i) External appearance, physical properties: Yellow oily matter
ii) UV, visible: $\lambda_{max}$=212 nm, $\epsilon_{max}$=8572
iii) IR(KBr) ν $cm^{-1}$: 3448, 3075, 3006, 2958, 2836, 2597, 2360, 2065, 1948, 1737, 1601, 1489
iv) $^1$H-NMR: 400 MHz ($CDCl_3$) δ ppm: 2.25 (s, 3H), 3.89 (s, 3H), 7.14 (dd, 1H, J=8.0, 8.0 Hz), 7.17~7.20 (m, 2H), 7.26 (dd, 2H, J=5.2, 7.2 Hz), 7.41 (dd, 1H, J=8.1, 8.1 Hz), 7.72 (td, 1H, J=1.2, 1.2 Hz), 7.83 (td, 1H, J=1.1, 7.6 Hz)
v) $^{13}$C-NMR; 100 MHz ($CDCl_3$) δ ppm: 164.72, 159.73, 149.56, 131.17, 130.78, 130.30, 129.63, 126.98, 126.09, 122.56, 121.98, 120.10. 114.55, 55.50, 16.23
vi) LREIMS m/z (%): 243 [100%, $M^+$+H]
vii) HRFABMS: With respect to $C_{15}H_{14}O_8$, Calculated value of ($M^+$+H) 243.0943; Measurement value of 243.1026.

Example 3

Synthesis of Compound CU-5008

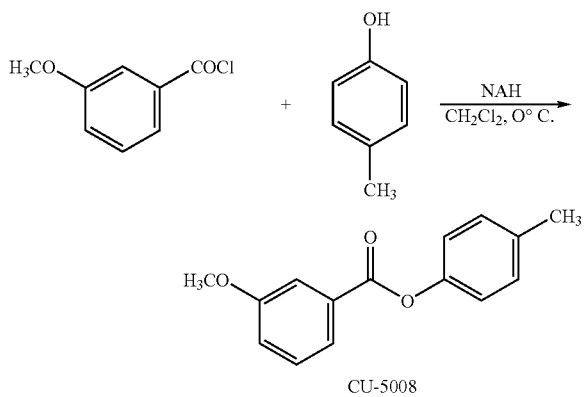

Synthesis Method

Sodium hydride (360 mg, 60 mass %, liquid paraffin suspension, 8.6 mmol) was poured in to a 100 mL round-bottomed flask, and dissolved in dichloromethane (10 mL) under an argon atmosphere. The resulting mixture was stirred at 0° C. Next, p-creosol (440 mg, 4.3 mmol) was added, and agitation at 0° C. performed for 5 minutes. Then, meta anisole chloride (610 mg, 4.3 mmol) was slowly added dropwise, and agitation at 0° C. performed for 1 hour. Destruction of the base material was confirmed using TLC, and then saturated chloride ammonium aqueous solution (10 mL) was added, and extraction performed twice using dichloromethane (70 mL). Following washing of the organic layer with saturated saline, anhydrous sodium sulfate was used for drying, and then the solvent was distilled off. 1.0 g of the obtained residue (a light yellow solid) was purified using silica-gel column chromatography ($SiO_2$ 20 g, ethyl acetate/n-hexane=10/1), and the obtained crystals were recrystallized from n-hexane, and compound CU-5008 (730 mg, yield 73%) obtained.

Physical Property Values and Spectrum Data:
i) External appearance, physical properties: m.p.=58 to 61° C.
ii) UV, visible: $\lambda_{max}$=212 nm, $\epsilon_{max}$=38055 $[\alpha]_D^{24}$=0.0 (c=0.98, CHCl$_3$)
iii) IR(KBr) $\nu$ cm$^{-1}$: 2971, 1725, 1601, 1508, 1277, 1200, 1088, 1030, 906, 752, 504
iv) $^1$H-NMR; 400 MHz (CDCl$_3$) $\delta$ ppm: 2.36 (s, 3H, PhCH$_3$), 3.87 (s, 3H, OCH$_3$), 7.06~7.81 (m, 8H, Ph)
v) $^{13}$C-NMR; 100 MHz (CDCl$_3$) $\delta$ ppm: 20.87, 55.47, 114.43, 120.06, 121.31, 122.54, 129.52, 130.00, 130.95, 135.49, 148.70, 159.65, 165.21
vi) LREIMS m/z (%): 242 [27%, M$^+$], 135 [100%]
vii) HRFABMS: With respect to C$_{15}$H$_{15}$O$_3$, Calculated value of (M$^+$+H) 243.1021; Measurement value of 243.1019.

Example 4

Synthesis of Compound CU-9005

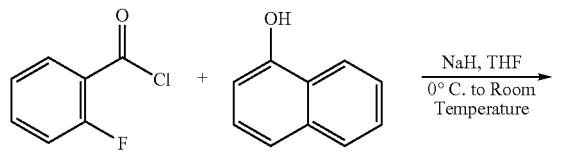

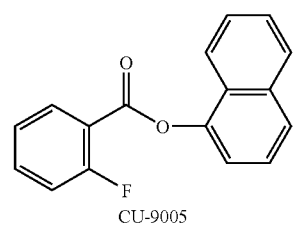

CU-9005

1-Naphthol (691 mg, 48 mmol) was weighed in a 100 mL round-bottomed flask, and argon substitution performed. Next, THF (40 mL, 1.0 M) is added, and cooling to 0° C. carried out. Sodium hydride (176 mg, 60 mass % liquid paraffin suspension, 4.4 mmol) and 2-fluorobenzyl chloride (634 mg, 4.0 mmol) were added to the THF solution, and stirred for 2 hours at room temperature. After TLC was used to confirm destruction of the base material, saturated saline (20 mL) was added, diethyl ether (20 mL×2) was used for extraction, and drying performed with anhydrous sodium sulfate. After filtering, the filtrate was distilled off under a reduced pressure, and then purifying was performed using silica-gel column chromatography (SiO$_2$ 30 g, ethyl acetate/n-hexane=1/20) to obtain compound CU-9005 (1.01 g, yield 95%).

Physical Property Values and Spectrum Data:
i) External appearance, physical properties: Yellow oily matter p0 ii) UV, visible: $\lambda_{max}$=221.00 nm (dichloromethane solvent), $\epsilon_{max}$=71679
iii) IR(neat) $\nu$ cm$^{-1}$: 3432, 3065, 1937, 1745, 1612, 1290, 1241, 754, 455
iv) $^1$H-NMR; 400 MHz (CDCl$_3$) $\delta$ ppm: 7.17~7.25 (m, 2H), 7.40 (dd, 1H, J=1.0, 7.5 Hz), 7.45~7.57 (m, 4H), 7.74 (d, 1H, J=8.1 Hz), 7.82~7.89 (m, 1H), 7.98~8.02 (m, 1H), 8.17 (dt, 1H, J=1.7, 7.5 Hz)

v) $^{13}$C-NMR: 55 MHz (CDCl$_3$) $\delta$ ppm: 117.0, 117.8, 118.1, 121.2, 124.1, 124.2, 125.3, 126.1, 126.4, 126.7, 127.9, 132.5, 134.6, 135.2, 135.3, 146.4, 160.9, 162.7, 163.5
vi) LREIMS m/z (%): 267 [100%, M$^+$+1]
vii) HRFABMS: With respect to C$_{17}$H$_{12}$O$_2$F, Calculated value of 267.0826; Measurement value of 267.0821.

Example 5

Synthesis of Compound CU-10005

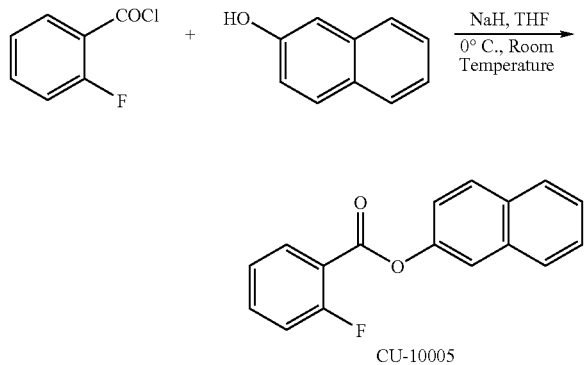

CU-10005

Synthesis Method

2-Naphthol (541.4 mg, 3.76 mmol) was weighed in a 100 mL round-bottomed flask, and argon substitution performed. Next, THF (30 mL) was added, and cooling to 0° C. carried out. Sodium hydride (180.3 mg, 60 mass % liquid paraffin suspension, 1.1 equivalent weight) and 2-fluorobenzyl chloride (0.54 mL, 1.2 equivalent weight) were added to the THF solution, and stirred for 30 minutes at room temperature. After TLC was used to confirm destruction of the base material, saturated chloride ammonium aqueous solution (5 mL) was added, and extracted with ethyl acetate (50 mL×2). Then, washing was performed using saturated saline and anhydrous sodium sulfate was used for drying. After filtering, the filtrate was distilled off under a reduced pressure, and a crude product was obtained as a white solid. The obtained product was recrystallized using n-hexane, and compound CU-10005 (0.95 g, yield 95%) was obtained.

Physical Property Values and Spectrum Data:
i) External appearance, melting point: White powder, m.p.=94 to 96° C. (n-hexane).
ii) UV, visible: $\lambda_{max}$=224.0 nm, $\epsilon_{max}$=108436
iii) IR(KBr) $\nu$ cm$^{-1}$: 1728, 1611, 1457, 1296, 1237, 1151, 755
iv) $^1$H-NMR; 400 MHz (CDCl$_3$) $\delta$ ppm: 7.24 (ddd, 1H, J=1.0, 8.4, 10.7 Hz), 7.30 (td, 1H, J=1.0, 7.6 Hz), 7.38 (dd, 1H, J=2.4, 8.9 Hz), 7.47~7.54 (m, 2H), 7.60~7.65 (m, 1H), 7.72 (d, 1H, J=12.2 Hz), 7.83~7.89 (m, 2H), 7.91 (d, 1H, J=8.9 Hz), 8.16 (td, 1H, J=1.8, 7.6 Hz)
v) $^{13}$C-NMR; 100 MHz (CDCl$_3$) $\delta$ ppm: 117.1, 117.4, 118.1, 118.7, 121.1, 124.1, 124.2, 125.8, 126.6, 127.7, 127.8, 129.5, 131.6, 132.6, 133.8, 135.2, 135.3, 148.3, 161.1, 162.9, 163.7
vi) LREIMS m/z (%): 266 [100%, M$^+$]
vii) HRFABMS: With respect to C$_{17}$H$_{11}$FO$_2$, Calculated value of 266.0743; Measurement value of 266.0761

Example 6

Synthesis of Compound CU-11005

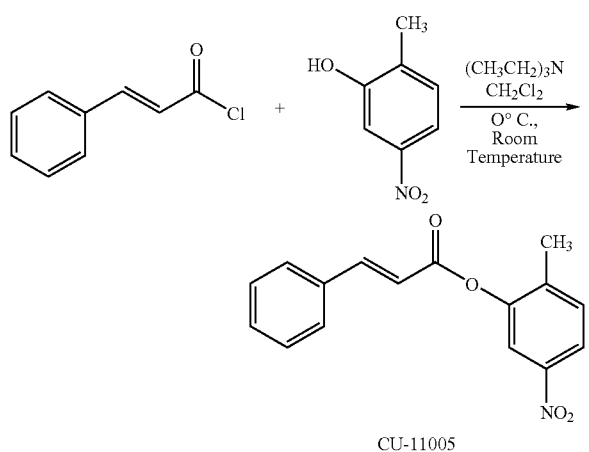

CU-11005

Synthesis Method

2-Methyl-5-nitrophenol (541 mg, 3.53 mmol) was poured into a 50 mL round-bottomed flask, and argon substitution performed. Next, dichloromethane (23 mL) was added to the flask, and stirred while ice cooling was performed. Triethylamine (0.59 mL, 4.24 mmol, 1.2 equivalent weight) was added to the flask, and then a dichloroethane (5 mL) solution of cinnamoyl chloride (883 mg, 5.3 mmol, 1.5 equivalent weight, trans=75%) was added dropwise over 5 minutes. Then, the resulting mixture was stirred for one hour while ice cooling was continued, and thereafter stirring at room temperature was performed for 30 minutes. Then, water (20 mL) was added and the reaction stopped. After the organic layer was removed, extraction was performed twice from the water layer using dichloroethane (20 mL), and the obtained organic layer was washed using saturated sodium hydrogencarbonate solution (20 mL) and brine (20 mL). This organic layer was dried using anhydrous sodium sulfate, and, following filtering, the solvent was distilled off under a reduced pressure, and 1.18 g of a white solid residue obtained.

The residue was recrystallized from a mixed solvent of ethyl acetate/n-hexane=1/10, and the compound CU-10005 (767.6 mg, yield 77%) was obtained as a mixture with trans/cis ratio of 5/1. Further, the mother liquid was purified using silica-gel column chromatography (acetic ethyl/n-hexane=1/10) to obtain compound CU-9005 (232 mg, yield 23%) as a mixture with trans/cis ratio of 5/1.

Physical Property Values and Spectrum Data:
i) External appearance, melting point: White solid, m.p=104 to 106° C.
ii) UV, visible: $\lambda_{max}$=283 nm, $\epsilon_{max}$=62200
iii) IR(KBr) ν $cm^{-1}$: 3440, 3083, 1730, 1634, 1523, 1347, 1142
iv) $^1$H-NMR; 400 MHz (CDCl$_3$, 27° C.) δ ppm: 2.33 (s, 3H, PhC$\underline{H}_3$), 6.54 (d, 0.15H, J=15 Hz, cis-CHCOO), 6.67 (d, 0.75H, J=16 Hz, trans-CHCOO), 7.42~7.46 (m, 3.75H, trans-Ar), 7.57~7.63 (m, 1.25H, cis-Ar), 7.86 (d, 0.15H, J=16 Hz, cis-Ar-CH), 7.93 (0.75H, J=16 Hz, trans-Ar-CH), 8.01~8.06 (m, 3H, Ar-OCO)
v) $^{13}$C-NMR; 100 MHz (CDCl$_3$, 27° C.) δ ppm: 76.78, 77.00, 115.97, 117.90, 120.91, 128.45, 128.57, 129.09, 131.12, 131.47, 133.82, 138.67, 147.89, 164.47
vi) LREIMS m/z (%): 283 [12%, M$^+$], 130 [100%, reference peak]
vii) HRFABMS: With respect to $C_{16}H_{14}NO_4$, Calculated value of [M$^+$+H] 284.0923; Measurement value of 284.0936

II. Evaluation of Skin Irritant Effect

Example 7

Blocking Effects Against UV Ray Irradiated on Guinea Pigs' Skin (1) Test Method Each compound of the present invention and commercially available p-methoxy cinnamic acid-2-ethyl hexyl as a positive reference were mixed with an ointment base (Plastibase), and 2.5% (mass % of active ingredient) and 5% ointment were prepared for each. The belly area of male Hartley guinea pigs that were 6 to 10 weeks old was shaved, and then further close shaved using an electric shaver. The test animals were then anaesthetized by injecting pentobarbital sodium (30 mg/kg) in their abdominal cavity. Then, 100 mg of the base material, 2.5% ointment and the 5% ointment were respectively spread in 6 to 7 cm long/15 cm wide areas of the shaved belly area of the test animal starting from its head. 10 minutes after spreading, the skin was covered with a piece of felt in which 9 holes (3×3) with 1 cm diameter had been made. A UV ray (3000 Lux) was then irradiated for a 90 second period. 24 hours after the irradiation, the intensity of the red circular marks that had been produced were observed, and the blocking effect investigated. Note that, the evaluation of the UV ray blocking effect was carried out in accordance with the following evaluation criteria (score based on 5 level evaluation).

Evaluation Criteria
0: No blocking effect
1: Slight blocking effect
2: Obvious blocking effect
3: Almost completely blocked
4: Completely blocked Accordingly, the total score is 24 if 6 irradiated sites are completely blocked.

(2) Test Results

In advance, 99 types of related compound were prepared using the test method described above as 10% ointments including the compounds of the present invention (the compounds expressed by formula I) and the compounds that are the active ingredient of the UV ray protection agent of the present invention (the compounds expressed by formula I'). A screening test was performed, and 9 compounds that 100% blocked the UV rays selected. Then, lower concentration ointments were prepared for these 9 compounds and an investigation was carried out to test the UV ray protection effect thereof. The results are shown in Table 1 below. Note that, as a reference compound, the results for p-methoxy cinnamic acid ethyl hexyl that is used as the active ingredient in commercially sold UV ray protection agents are also shown.

As shown in Table 1, all of the compounds demonstrate effective UV ray protection effect. Among them, compound CU-9005 shows the strongest UV ray protection effect, and then compounds CU-2010, CU-5004, and CU-5009 in that order. These results suggest a UV ray blocking effect that is comparable or superior to that of the reference compound p-methoxy cinnamic acid ethyl hexyl. Accordingly, it can be judged that any of these compounds can be used as an active ingredient for UV ray protection agents.

TABLE 1

UV Ray Protection Effect of Each Compound

| Compound | UV ray blocking effect score[4] |
|---|---|
| CU-1008 (Example 1)[1] | 20 |
| CU-2102 (Example 2)[1] | 15 |
| CU-5008 (Example 3)[1] | 13 |
| CU-9005 (Example 4)[1] | 24 |
| CU-10005 (Example 5)[1] | 7 |
| CU-11005 (Example 6)[1] | 12 |
| CU-2010 (known compound)[2] | 21 |
| CU-5004 (known compound)[2] | 20 |
| CU-5009 (known compound)[2] | 19 |
| p-Methoxy-cinnamic acid-2-ethyl hexyl[3] | 18 |

[1]: Compound expressed by formula I
[2]: Compound expressed by formula I'
[3]: Control compound
[4]: Score for complete blocking by 2.5% and 5% ointments = 24

Note that, 24 hours after testing, there was no sign whatsoever of abnormality on the skin of the guinea pigs on which each 100 mg of compound 10% ointment had been spread. Accordingly, it can be judged that there is no skin irritant effect.

Example 8

Safety of Each Compound for Mice

An investigation was carried out using 5 week old male ddY mice. From among the compounds that clearly demonstrated strong UV ray protection effects in the Seventh Example, compounds CU-5004, CU-5008, CU-5009, and CU-10005 were selected, and acute toxicity was investigated by injecting them under the skin of the mice.

Each compound (250 mg) was placed in suspension using the same amount of Tween-80, and then diluted with physiologic saline (5 mL) to form a 5% suspension. Then, supersonic treatment was performed to create the specimen. 0.2 mL/10 g (1 g/kg) of the specimen was injected per body weight under the skin of the back portion of each mouse in groups of five mice. The behavior of the mice was then observed for 1 week after injection while the mice were fed. The body weight of the mice was measured on the 1st, 3rd, 6th and 7th days. After one week, an abdominal section was performed, and changes in the various internal organs and abnormality of the injected area checked for.

(2) Test Results

As shown in Table 2 below, there were no cases of any mouse in any group dying after the injection. Further, there were no abnormalities in terms of spontaneous movement, nor any changes resulting from toxicity in their general symptoms.

In the group injected with compound CU-10005, the body weight of the mice increased following injection in the same manner as the body weight of the mice in a reference group that was not injected with any substance.

In the groups injected with compound CU-5004, CU-5008 and CU-5009, the body weight of the mice decreased following injection in all cases. However, by the 7th day following injection, the body weight of the mice had recovered to its level at the time of the first injection.

Moreover, in a post-mortem examination conducted on the 7th day after injection, there was no abnormality of the internal organs, and no tissue changes resulting from the respective compounds was observed. Accordingly, acute toxicity resulting from a single under skin injection of the respective compounds was extremely low, and the $LD_{50}$ values in all cases were 1 g/kg or above.

TABLE 2

Acute Toxicity Resulting from Single Under Skin Injection in Mice (Injection Amount: 1 g/kg)

| Compound | Injection amount | Case of death | $LD_{50}$ | Observed items |
|---|---|---|---|---|
| CU-5004[2] | 1 g/kg | 0/5 | 1 g/kg or more | Weight reduction |
| CU-5008[1] | 1 g/kg | 0/5 | 1 g/kg or more | Weight reduction |
| CU-5009[2] | 1 g/kg | 0/5 | 1 g/kg or more | Weight reduction |
| CU-10005[1] | 1 g/kg | 0/5 | 1 g/kg or more | No abnormalities |

As described previously, in the Seventh Example, after 100 mg of the present compounds were applied to the guinea pigs in 10% ointments (20 to 25 mg/kg body weight), the occurrence of localized effects on the skin was not observed during the 24 hour period after application, and no skin irritation effects were apparent. Moreover, as shown in Example Eight, the safety of the compounds is high since the lethal dose 50% of the mouse under skin injection is respectively equal to or above 1 g/kg. Accordingly, the compounds have a high degree of usability.

INDUSTRIAL APPLICABILITY

The UV ray protection effect of the compounds of the present invention and the UV ray protection agent of the present invention are, in terms of strength, equal to or better than those of sunscreen creams that are commercially available, and also have a high degree of safety. Accordingly, the compounds of the present invention and the UV ray protection agent of the present invention are suitable for products that are directly applied to the skin to block UV rays such as cosmetic products, and various types of preparations for quasi-drugs, etc. Further, the compounds and the UV ray protection agent of the present invention may be used by applying them or mixing them with various types of products for absorbing or blocking UV rays, such as textile fabrics, non-woven fabrics, plastic products like plastic films and sheets, rubber products, and paints. Moreover, the compounds and UV ray protection agent may be injected, impregnated or mixed into materials used for building in order to prevent the damage caused by UV rays.

What is claimed is:

1. A compound expressed by the following formula:

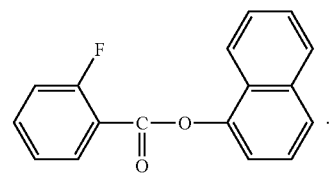

2. A compound expressed by the following formula:

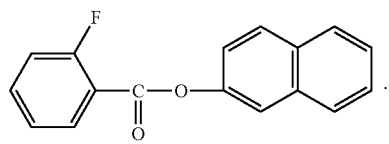

3. A compound expressed by the following formula:
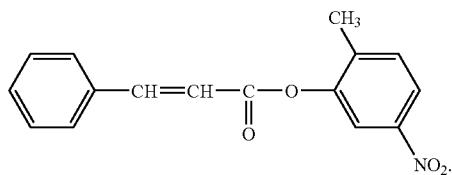
4. An ultraviolet ray protection agent including as an active ingredient the compound of claim 1.
5. An ultraviolet ray protection agent including as an active ingredient the compound of claim 2.
6. An ultraviolet ray protection agent including as an active ingredient the compound of claim 3.
* * * * *